(12) United States Patent
Yamano et al.

(10) Patent No.: US 8,393,218 B2
(45) Date of Patent: Mar. 12, 2013

(54) ULTRASONIC TESTING METHOD AND APPARATUS

(75) Inventors: Masaki Yamano, Osaka (JP); Masami Ikeda, Osaka (JP); Kenji Fujiwara, Osaka (JP); Hiroshi Kubota, Osaka (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 39 days.

(21) Appl. No.: 13/129,859

(22) PCT Filed: Nov. 18, 2009

(86) PCT No.: PCT/JP2009/069536
§ 371 (c)(1),
(2), (4) Date: Aug. 5, 2011

(87) PCT Pub. No.: WO2010/058783
PCT Pub. Date: May 27, 2010

(65) Prior Publication Data
US 2011/0283798 A1 Nov. 24, 2011

(30) Foreign Application Priority Data

Nov. 19, 2008 (JP) ................................. 2008-296124

(51) Int. Cl.
*G01N 29/00* (2006.01)
(52) U.S. Cl. .................. 73/632; 73/592; 73/599; 73/622
(58) Field of Classification Search .................... 73/632, 73/592, 596, 599, 600, 602, 620, 622, 628
See application file for complete search history.

(56) References Cited

U.S. PATENT DOCUMENTS

| 3,156,110 | A | * | 11/1964 | Clynes | 73/628 |
| 4,459,853 | A | * | 7/1984 | Miwa et al. | 73/626 |
| 5,426,978 | A | * | 6/1995 | Imai | 73/622 |
| 8,266,964 | B2 | * | 9/2012 | Iizuka et al. | 73/592 |
| 8,266,966 | B2 | * | 9/2012 | Ichigo et al. | 73/606 |
| 2011/0283798 | A1 | * | 11/2011 | Yamano et al. | 73/632 |
| 2012/0167690 | A1 | * | 7/2012 | Yamano | 73/632 |

FOREIGN PATENT DOCUMENTS

| JP | 62-254052 | 11/1987 |
| JP | 3-26958 | 2/1991 |
| JP | 09-229918 | 9/1997 |
| JP | 10-153587 | 6/1998 |
| JP | 3674131 | 7/2005 |
| WO | 2007/024000 | 3/2007 |

* cited by examiner

*Primary Examiner* — J M Saint Surin
(74) *Attorney, Agent, or Firm* — Clark & Brody

(57) ABSTRACT

An ultrasonic testing apparatus 100 comprises an ultrasonic probe 1 including n (n≧2) number of transducers arranged along a predetermined direction, disposed so as to face a test object P, and a transmission/reception control device 2 for selecting m (n>m≧1) number of transducers from among the n number of transducers, transmitting ultrasonic waves from the selected m number of transducers toward the test object, receiving the ultrasonic waves therefrom, and switched m number of transducers to b selected successively. If an angle that the arrangement direction of the transducers makes with the surface of the test object which ultrasonic waves enter is θ, and the effective beam width of each selected m number of transducers with respect to a target flaw is W1, the transmission/reception control device switches m number of transducers to be selected successively by a switching pitch length P satisfying the formula: P≦W1·cos θ.

6 Claims, 12 Drawing Sheets

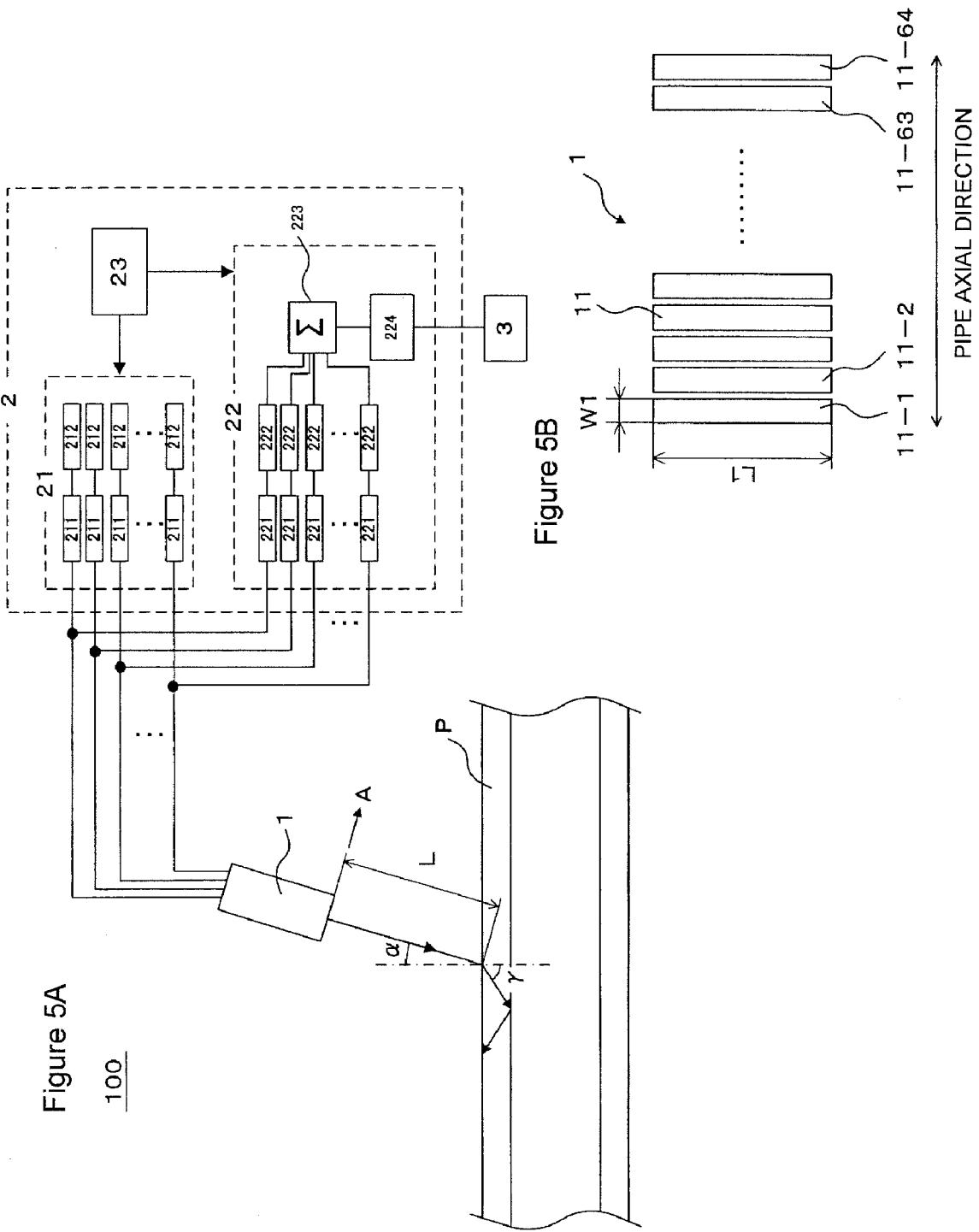

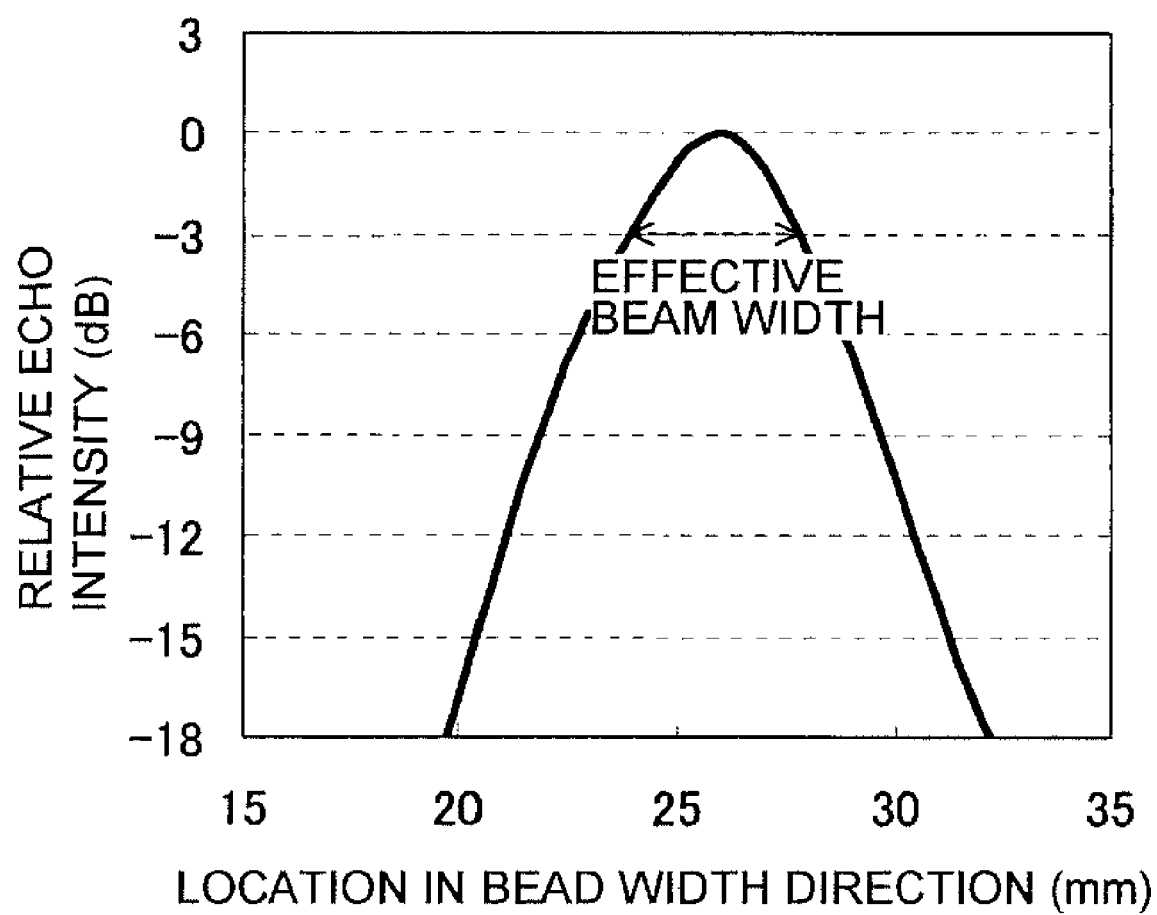

(STEP1)

11A  11B  11A (STEP2)

(STEP3)

ULTRASONIC TESTING METHOD AND APPARATUS

TECHNICAL FIELD

The present invention relates to an ultrasonic testing method and apparatus capable of accurately detecting various flaws present in test objects such as pipe or tube. More particularly, it relates to an ultrasonic testing method and apparatus capable of easily setting the proper switching pitch for transducers for accurately detecting target flaws when a test object is tested by using an ultrasonic probe including a plurality of transducers.

BACKGROUND ART

In ultrasonic testing of pipe or tube (Hereinafter, "pipe or tube" is referred to as a pipe when deemed appropriate.), it is necessary to detect not only an axial flaw (a flaw extending in the axial direction of pipe) but also a circumferential flaw (a flaw extending in the circumferential direction of pipe) and a planar flaw parallel with the inner and outer surfaces of pipe called a lamination.

The axial flaw is detected by transmitting and receiving ultrasonic waves by using an ultrasonic probe 1' tilted in the circumferential direction of a pipe P and by propagating ultrasonic shear waves in the circumferential direction of the pipe P as shown in FIG. 1A.

Also, the circumferential flaw is detected by transmitting and receiving ultrasonic waves by using an ultrasonic probe 1' tilted in the axial direction of the pipe P and by propagating ultrasonic shear waves in the axial direction of the pipe P as shown in FIG. 1B.

Further, the lamination is detected by propagating ultrasonic longitudinal waves in the wall thickness direction of pipe as shown in FIG. 1C.

Thus, to detect various flaws that extend in different directions or have different shapes, a plurality of ultrasonic probes are generally used according to the type of flaw.

Conventionally, for a flaw of any of the types mentioned above, as shown in FIG. 2, ultrasonic testing has been performed by using a plurality of ultrasonic probes 1' (in the example shown in FIG. 2, four ultrasonic probes denoted by symbols A1 to A4) arranged along the axial direction of pipe to enhance the testing efficiency and by transmitting and receiving ultrasonic waves from/by the ultrasonic probes 1' and conveying the pipe in the axial direction while the pipe is rotated in the circumferential direction (spiral conveyance). For example, the ultrasonic probe A1 tests the pipe in a spiral region hatched in FIG. 2, and the ultrasonic probe A2 tests the pipe in a spiral region shaded in FIG. 2. Thus, by arranging the plurality of ultrasonic probes 1' along the axial direction of pipe, whole surface testing of pipe has been realized.

However, the conventional ultrasonic testing method shown in FIG. 2 has a problem that the flaw detectability is deteriorated because of the decrease in sound field intensity at the boundary of sound fields formed by the adjacent ultrasonic probes 1'. FIG. 3 shows a profile example of echo intensity from a circumferential flaw formed on a pipe by machining. Specifically, FIG. 3 is a graph in which the flaw echo intensities obtained with the ultrasonic probes A1 to A4 by moving the pipe, on which a circumferential flaw has been formed, in the axial direction correspond to the axial location of the circumferential flaw. FIG. 3 reveals that in the boundary portion of the adjacent ultrasonic probes 1' (the portion encircled by a broken line in FIG. 3), the flaw echo intensity decreases markedly. Therefore, it is apparent that the flaw detectability is also markedly deteriorated in this boundary portion.

To solve the above problem, for example, a technique described in JP3674131B (Patent Document 1) has been proposed. In the technique described in Patent Document 1, a plurality of ultrasonic probes are arranged in a straight line, and from among the plurality of ultrasonic probes, a probe group consisting of a fixed number of continuous ultrasonic probes is selected to transmit and receive ultrasonic waves, the probe group to be selected being switched successively. This technique is characterized in that the switching pitch is matched to the total width of a plurality of ultrasonic probes, and is set so as to be equal to or smaller than the practical effective beam width of the ultrasonic wave emitted from one selected probe group.

The "practical effective beam width" is defined as a width until the level is decreased by 3 dB with respect to the peak value of sound field intensity obtained in the central portion of ultrasonic probe (paragraph 0005 of Patent Document 1). That is to say, the "practical effective beam width" is a value determined from the profile of sound field intensity of the ultrasonic beam transmitted from the ultrasonic probe.

However, when the technique described in Patent Document 1 is applied to testing of a pipe whose various flaws extend in different directions or have different shapes must be detected, a problem described below arises.

The profile of flaw echo intensity obtained when the ultrasonic probes are scanned in the arrangement direction thereof (in the example shown in FIG. 2, the axial direction of pipe) cannot be determined uniquely by only the profile of sound field intensity, and the flaw shape in the scanning direction of the ultrasonic probe exerts a great influence.

FIG. 4 shows a profile example of flaw echo intensity obtained when the identical ultrasonic probe is scanned in the axial direction of pipe with respect to an axial flaw and a circumferential flaw produced on the pipe.

In the above-described example, since the identical ultrasonic probe is used, the profile of sound field intensity is the same. However, as shown in FIG. 4, if the flaw is different, the profile of flaw echo intensity will be different. Therefore, with the practical effective beam width derived from the profile of sound field intensity, the switching pitch cannot be determined properly, and the flaw may be overlooked. Consequently, there arises a problem that the switching pitch must be determined inevitably by repeating trial and error for each type of flaw.

DISCLOSURE OF THE INVENTION

The present invention has been made to solve the above problems with the prior art, and accordingly an object thereof is to provide an ultrasonic testing method and apparatus capable of easily setting the proper switching pitch for transducers that is proper for accurately detecting target flaws when a test object is tested by using an ultrasonic probe including a plurality of transducers.

In order to solve the above-mentioned problem, as described in claim 1, the present invention provides an ultrasonic testing method, comprising: a disposing step of disposing an ultrasonic probe including n (n≧2) number of transducers arranged along a predetermined direction so as to face a test object; a testing step of testing the test object by selecting m (n>m≧1) number of transducers from among the n number of transducers, transmitting ultrasonic waves from the selected m number of transducers toward the test object and receiving the ultrasonic waves therefrom; and a scanning step of switching m number of transducers to be selected successively, the method repeating the testing step and the scanning step alternately, thereby ultrasonic testing the test object, wherein, in the scanning step, if an angle that the arrangement direction of the n number of transducers makes with the surface of the test object which ultrasonic waves enter is θ(°), and the effective beam width of each selected m number of transducers with respect to a target flaw is W1 (mm), m number of transducers to be selected are switched successively by a switching pitch length P (mm) satisfying the following formula (1):

$$P \leq W1 \cdot \cos \theta \quad (1)$$

and, in the testing step, the test object is tested with testing sensitivity adjusted beforehand for each selected m number of transducers so that the highest echo intensities from target flaws received by each selected m number of transducers are approximately equivalent.

In the present invention, "an angle that the arrangement direction of the n number of transducers makes with the surface of the test object which ultrasonic waves enter" means an angle that the arrangement direction of the n number of transducers makes with the tangential plane of the test object at the incident point of ultrasonic waves in the case where the test object is a material having a substantially circular cross section, such as a pipe.

Also, in the present invention, "the effective beam width of each selected m number of transducers with respect to a target flaw" means a length of a range (a range along the surface of test object at the incident point of ultrasonic waves) in which flaw echo intensity is not lower than a predetermined intensity (for example, −3 dB when the maximum intensity is set at 0 dB) in the profile of echo intensity from a target flaw that is obtained when each selected m number of transducers is scanned in the transducer arrangement direction.

Further, in the present invention, "a switching pitch length" means a pitch of the adjacent m number of transducers to be selected (the pitch in the transducer arrangement direction, in units of length).

According to the present invention, in the scanning step, m number of transducers to be selected are switched successively by the switching pitch length P (mm) satisfying formula (1). In other words, m number of transducers to be selected are switched successively so that the range of the effective beam width of each selected m number of transducers for a target flaw (the range having a length corresponding to the effective beam width where the center of each selected m number of transducers provides the reference) has an overlapped portion. For this reason, even if a target flaw is present at any location in the testing region of ultrasonic probe, the target flaw is located in the range of the effective beam width of any selected m number of transducers. Therefore, the echo intensity from the target flaw is not lower than a predetermined intensity (for example, −3 dB when the maximum value of flaw echo intensity obtained with the selected transducers is set at 0 dB).

Also, according to the present invention, in the testing step, the test object is tested with testing sensitivity (amplification degree of echo intensity) adjusted beforehand for each selected m number of transducers so that the highest echo intensities from target flaws received by each selected m number of transducers are approximately equivalent. As described above, the target flaw is located in the range of the effective beam width of any selected m number of transducers in which the testing sensitivity is regulated so that the highest echo intensities are approximately equivalent. Therefore, even if the echo from a target flaw is detected by any selected m number of transducers (in other words, even if a target flaw is present at any location in the testing region of ultrasonic probe), a flaw echo intensity not lower than the predetermined intensity (for example, −3 dB when the maximum value of flaw echo intensity obtained with the ultrasonic probe is set at 0 dB) can be obtained, so that a target flaw can be detected with high accuracy.

As described above, according to the present invention, by setting the switching pitch length P (mm) of m number of transducers to be selected satisfying formula (1), a target flaw can be detected with high accuracy. That is to say, the conventional trial and error need not be repeated, and the switching pitch length P (mm) satisfying formula (1) has only to be selected, so that a proper switching pitch for transducer can be set easily in detecting a target flaw with high accuracy.

Preferably, as described in claim 2, in case that the n number of transducers included in the ultrasonic probe are arranged at an equal arrangement pitch of d (mm), in the scanning step, if an angle that the arrangement direction of the n number of transducers makes with the surface of the test object which ultrasonic waves enter is θ(°), and the effective beam width of each selected m number of transducers with respect to a target flaw is W1 (mm), m number of transducers to be selected are switched successively by a switching pitch number K satisfying the following formula (2):

$$K \leq W1 \cdot \cos \theta / d \quad (2).$$

In the present invention, "a switching pitch number" means a value obtained by converting the pitch of the adjacent m number of transducers to be selected (the pitch in the transducer arrangement direction) into the number of transducers. Therefore, the switching pitch number K is a positive integer.

Also, in order to solve the above-mentioned problem, as described in claim 3, the present invention provides an ultrasonic testing method, the method disposing a first ultrasonic probe for detecting an axial flaw which is possible to occur in a pipe or tube as a test object, a second ultrasonic probe for detecting a circumferential flaw which is possible to occur in the pipe or tube, and a third ultrasonic probe for detecting a lamination which is possible to occur in the pipe or tube, so as to face the pipe or tube, and while rotating the pipe or tube in the circumferential direction and relatively moving the first to third ultrasonic probes in the axial direction of the pipe or tube, transmitting ultrasonic waves from transducers included in the first to third ultrasonic probes toward the pipe or tube and receiving the ultrasonic waves therefrom, thereby ultrasonic testing the pipe or tube, wherein at least one ultrasonic probe selected from among the first to third ultrasonic probes is the ultrasonic probe according to claim 1 or 2, the arrangement direction of n number of transducers included in the selected ultrasonic probe is aligned with the axial direction of the pipe or tube, and the ultrasonic testing method according to claim 1 or 2 is carried out for the selected ultrasonic probe, and wherein the amount of relative displacement in the axial direction of the pipe or tube of the first to third ultrasonic probes per one turn of the pipe or tube is set so as to be not larger than the minimum substantial effective beam width of the substantial effective beam widths of the first to third ultrasonic probes in the axial direction of the pipe or tube for a target flaw.

In the present invention, for the ultrasonic probe of claim 1 or 2, "the substantial effective beam width" means a range (a range along the surface of test object at the incident point of ultrasonic waves) in which the profiles of echo intensity from a target flaw that is obtained for above-described each selected m number of transducers are combined, and in the combined echo intensity profile, the flaw echo intensity is not lower than the predetermined intensity (for example, −3 dB when the highest intensity is set at 0 dB).

Also, in the present invention, for the ultrasonic probe including a single transducer, "the substantial effective beam width" means a range (a range along the surface of test object at the incident point of ultrasonic waves) in which in the echo intensity profile of the target flaw that is obtained when the ultrasonic probe is scanned, the flaw echo intensity is not lower than the predetermined intensity (for example, −3 dB when the highest intensity is set at 0 dB).

According to the present invention, the amount of relative displacement in the axial direction of the pipe or tube of the first to third ultrasonic probes per one turn of the pipe or tube is set so as to be not larger than the minimum substantial effective beam width of the substantial effective beam widths in the axial direction of the pipe or tube for a target flaw of the first to third ultrasonic probes. Therefore, even if a target flaw is present in any portion of pipe or tube, for all of the first to third ultrasonic probes, the echo intensity from the target flaw is not lower than the predetermined intensity. As a result, all of axial flaw, circumferential flaw, and lamination can be detected with high accuracy.

Also, in order to solve the above-mentioned problem, as described in claim 4, the present invention provides an ultrasonic testing apparatus, comprising: an ultrasonic probe including n (n≧2) number of transducers arranged along a predetermined direction, disposed so as to face a test object; and a transmission/reception control device for selecting m (n>m≧1) number of transducers from among the n number of transducers, transmitting ultrasonic waves from the selected m number of transducers toward the test object and receiving the ultrasonic waves therefrom, and switching m number of transducers to be selected successively, wherein, if an angle that the arrangement direction of the n number of transducers makes with the surface of the test object which ultrasonic waves enter is) θ(°), and the effective beam width of each selected m number of transducers with respect to a target flaw is W1 (mm), the transmission/reception control device switches m number of transducers to be selected successively by a switching pitch length P (mm) satisfying the following formula (1):

$$P \leq W1 \cdot \cos \theta \quad (1)$$

and, in the transmission/reception control device, testing sensitivity is adjusted beforehand for each selected m number of transducers so that the highest echo intensities from target flaws received by each selected m number of transducers are approximately equivalent.

Preferably, as described in claim 5, in case that the n number of transducers included in the ultrasonic probe are arranged at an equal arrangement pitch of d (mm), if an angle that the arrangement direction of the n number of transducers makes with the surface of the test object which ultrasonic waves enter is θ(°), and the effective beam width of each selected m number of transducers with respect to a target flaw is W1 (mm), the transmission/reception control device switches m number of transducers to be selected successively by a switching pitch number K satisfying the following formula (2):

$$K \leq W1 \cdot \cos \theta / d \quad (2).$$

Further, in order to solve the above-mentioned problem, as described in claim 6, the present invention provides an ultrasonic testing apparatus, comprising: a first ultrasonic probe disposed so as to face a pipe or tube which is a test object, for detecting an axial flaw which is possible to occur in the pipe or tube; a second ultrasonic probe disposed so as to face the pipe or tube for detecting a circumferential flaw which is possible to occur in the pipe or tube; a third ultrasonic probe disposed so as to face the pipe or tube for detecting a lamination which is possible to occur in the pipe or tube; a first transmission/reception control device for transmitting ultrasonic waves from a transducer included in the first ultrasonic probe toward the pipe or tube and receiving the ultrasonic waves therefrom; a second transmission/reception control device for transmitting ultrasonic waves from a transducer included in the second ultrasonic probe toward the pipe or tube and receiving the ultrasonic waves therefrom; a third transmission/reception control device for transmitting ultrasonic waves from a transducer included in the third ultrasonic probe toward the pipe or tube and receiving the ultrasonic waves therefrom; and a driving device for rotating the pipe or tube in the circumferential direction and relatively moving the first to third ultrasonic probes in the axial direction of the pipe or tube, wherein at least one ultrasonic probe selected from among the first to third ultrasonic probes is the ultrasonic probe according to claim 4 or 5, and the arrangement direction of n number of transducers included in the selected ultrasonic probe is aligned with the axial direction of the pipe or tube; the transmission/reception control device corresponding to the selected ultrasonic probe of the first to third transmission/reception control devices is the transmission/reception control device according to claim 4 or 5; and the driving device rotates the pipe or tube in the circumferential direction and relatively moves the first to third ultrasonic probes in the axial direction of the pipe or tube so that the amount of relative displacement in the axial direction of the pipe or tube of the first to third ultrasonic probes per one turn of the pipe or tube is not larger than the minimum substantial effective beam width of the substantial effective beam widths of the first to third ultrasonic probes in the axial direction of the pipe or tube for a target flaw.

According to the present invention, when a test object is tested by using the ultrasonic probe including the plurality of transducers, a proper switching pitch for transducer can be set easily in detecting a target flaw with high accuracy.

BRIEF DESCRIPTION OF THE DRAWINGS

FIGS. 5A and 5B give schematic views showing a schematic configuration of an ultrasonic testing apparatus in accordance with a first embodiment of the present invention;

FIG. 9 is a diagram showing a profile example of echo intensity from a target flaw that is obtained when selected m number of transducers included in the ultrasonic probe shown in FIGS. 8A to 8C are scanned along the arrangement direction thereof;

BEST MODE FOR CARRYING OUT THE INVENTION

Figure 1A:
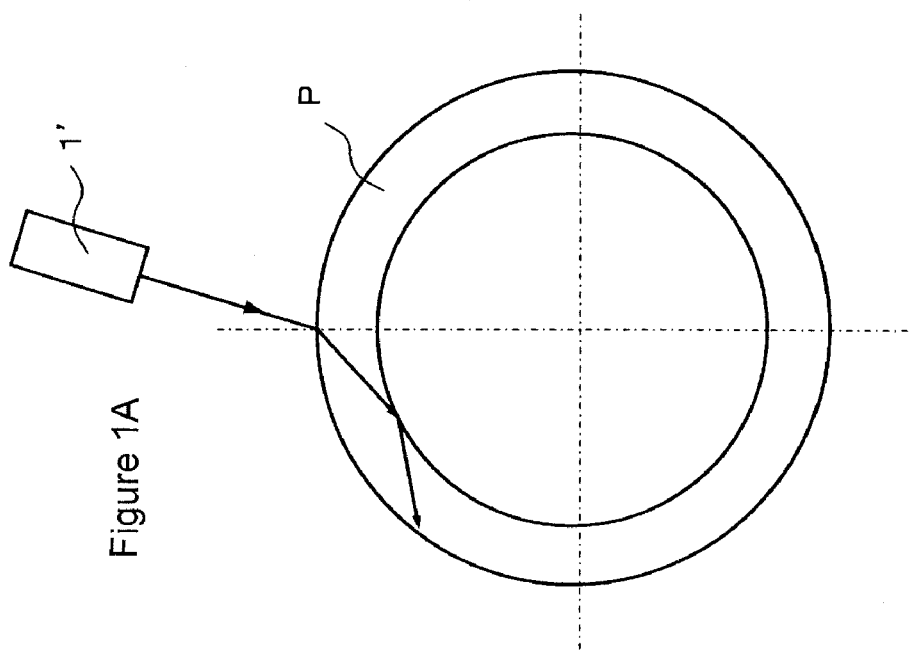
FIGS. 1A to 1C give explanatory views for explaining an ultrasonic testing method for various flaws present in a pipe.
Figure 1B:
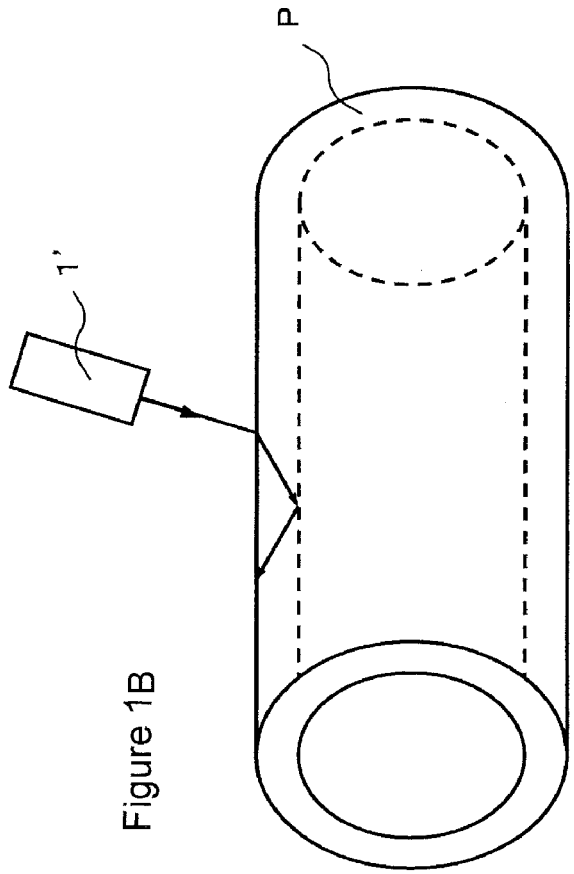
Figure 1C:
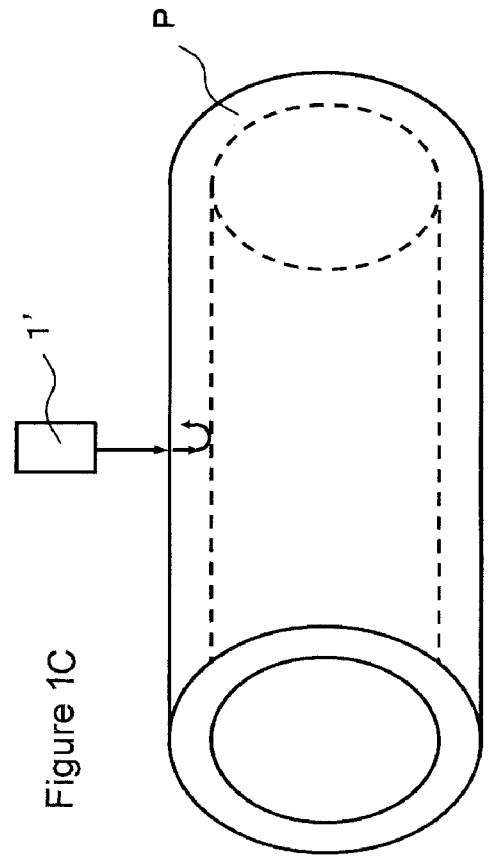
Figure 2:
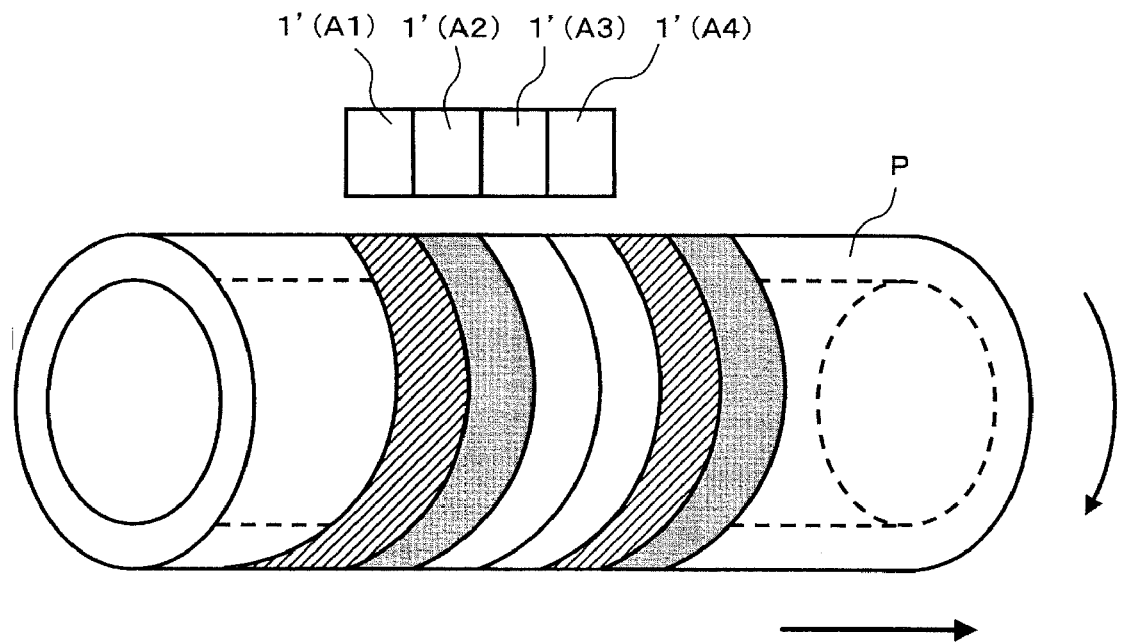
FIG. 2 is an explanatory view for explaining a conventional ultrasonic testing method.
Figure 3:
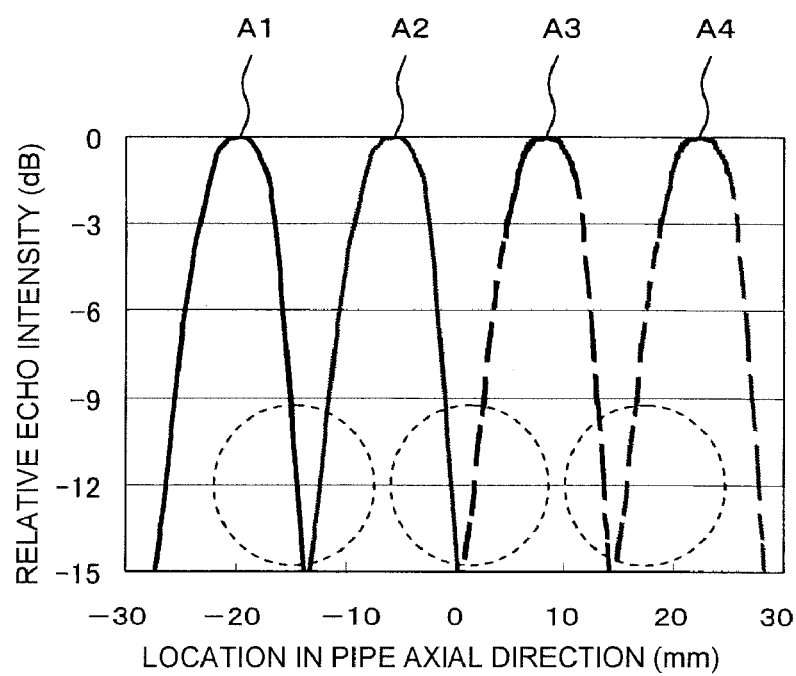
FIG. 3 is a diagram showing a profile example of echo intensity from a circumferential flaw that is obtained by the ultrasonic testing method shown in FIG. 2.
Figure 4:
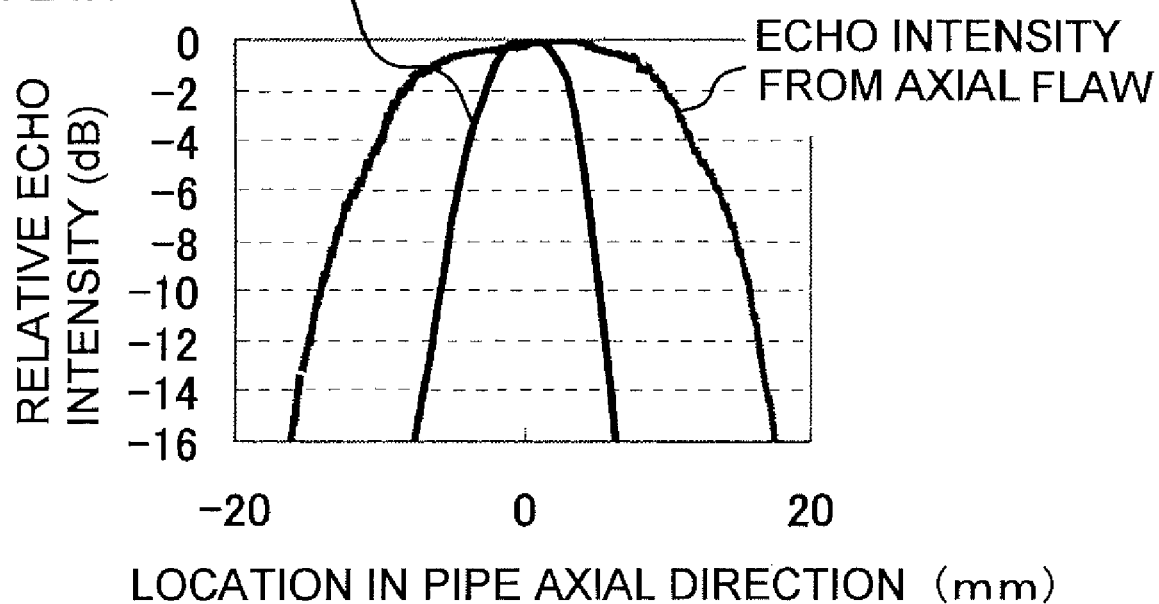
FIG. 4 is a diagram showing a profile example of flaw echo intensity that is obtained when the identical ultrasonic probe is scanned in the axial direction of a steel pipe with respect to an axial flaw and a circumferential flaw produced on the pipe.

An embodiment of the present invention will now be described with appropriate reference to the accompanied drawings by citing the case where a test object is a pipe.

<First Embodiment>

FIG. 5A and 5B give schematic views showing a schematic configuration of an ultrasonic testing apparatus in accordance with a first embodiment of the present invention, FIG. 5A being a front view (a sectional view of the pipe), and FIG. 5B being an enlarged plan view of an ultrasonic probe shown in FIG. 5A (an enlarged plan view in a state in which the ultrasonic probe is not tilted).

An ultrasonic testing apparatus 100 in accordance with this embodiment is an ultrasonic testing apparatus for detecting circumferential flaws. As shown in FIGS. 5A and 5B, the ultrasonic testing apparatus 100 in accordance with this embodiment comprises an ultrasonic probe 1 including 64 transducers 11 (11-1 to 11-64) arranged along the axial direction of a pipe P, disposed so as to face the pipe P. Also, the ultrasonic testing apparatus 100 in accordance with this embodiment comprises a transmission/reception control device 2 for selecting 30 transducers 11 (in this embodiment, a set of 30 transducers 11 is called transducer group) from among the 64 transducers 11, transmitting ultrasonic waves from the selected transducer group toward the pipe P, receiving the ultrasonic waves therefrom, and switching transducer group to be selected successively. Also, the ultrasonic testing apparatus 100 in accordance with this embodiment comprises a flaw evaluation section 3 that detects a flaw present in the pipe P by comparing the output signal sent from the transmission/reception control device 2 with a predetermined threshold value. Further, the ultrasonic testing apparatus 100 in accordance with this embodiment comprises a driving device (not shown) for rotating the pipe P in the circumferential direction and relatively moving the ultrasonic probe 1 in the axial direction of the pipe P.

The ultrasonic probe 1 of this embodiment is disposed separated from the pipe P by a distance of L=70 mm. Also, the ultrasonic probe 1 is disposed tilted by an angle of $\alpha \approx 19°$ in the axial direction of the pipe P from the normal to the surface of the pipe P (so that the angle of incidence a of ultrasonic wave is approximately equal to 19°. Thereby, ultrasonic shear waves having an angle of refraction γ of 45° are propagated along the axial direction of the pipe P. The testing frequency of the ultrasonic probe 1 of this embodiment is set at 5 MHz.

Each of the transducers 11 included in the ultrasonic probe 1 of this embodiment is a transducer having the same rectangular shape, and the transducers 11 are arranged in a straight line in the axial direction of the pipe P. Each of the transducers 11 of this embodiment has a length of L1=10 mm and a width of W1=0.4 mm, and the transducers 11 are arranged with a gap of 0.1 mm being provided therebetween. This means that the arrangement pitch for the transducers 11 in the axial direction of the pipe P is 0.5 mm.

The transmission/reception control device 2 of this embodiment comprises a transmission section 21, a reception section 22, and a control section 23.

The transmission section 21 includes pulsers 211 connected to the transducers 11 to supply a pulse signal for transmitting ultrasonic waves from the transducers 11, and delay circuits 212 for setting the delay time (transmission delay time) for the pulse signal supplied from the pulser 211 to the transducer 11.

The reception section 22 includes receivers 221 connected to the transducers 11 to amplify an echo received by the transducer 11, delay circuits 222 for setting the delay time (reception delay time) for the echo amplified by the receiver 221, a waveform synthesis circuit 223 for synthesizing the echoes sets the delay time for which has been set by the delay circuit 222, and an amplifier 224 for amplifying the echo synthesized by the waveform synthesis circuit 223. The amplification degree (testing sensitivity) of the amplifier 224 is adjusted beforehand for each selected transducer group so that the highest echo intensities from target flaws received by each selected transducer group switched by the control section 23 are approximately equivalent, as described later.

The control section 23 successively switches transducer group to be selected for transmitting and receiving ultrasonic waves selected from among the arranged 64 transducers 11. At this time, if an angle that the arrangement direction of the transducers 11 (the direction indicated by an arrow mark A in FIG. 5A) makes with the surface of the pipe P which ultrasonic waves enter (the tangential plane of the pipe P at the incident point of ultrasonic waves) is θ(°), and the effective beam width of each selected transducer group with respect to a target flaw is W1 (mm), the control section 23 successively switches transducer group to be selected by a switching pitch length P (mm) satisfying the following formula (1):

$$P \leq W1 \cdot \cos \theta \quad (1).$$

In particular, in the case where the 64 transducers 11 included in the ultrasonic probe 1 are arranged at an equal arrangement pitch of d (mm) as in this embodiment, the control section 23 successively switches transducer group to be selected by a switching pitch number K, satisfying the following formula (2):

$$K \leq W1 \cdot \cos \theta / d \quad (2).$$

Figure 6A:
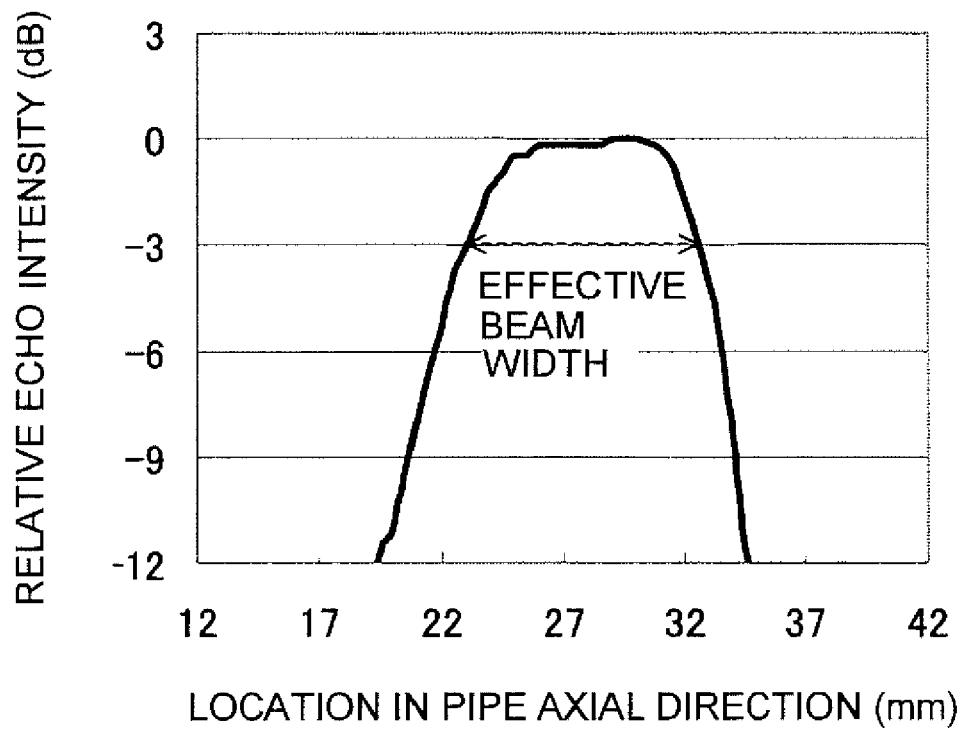
FIG. 6A and 6B give diagrams showing profile examples of echo intensity from a target flaw that is obtained when selected m number of transducers included in the ultrasonic probe shown in FIGS. 5A and 5B are scanned along the arrangement direction thereof.
Figure 6:
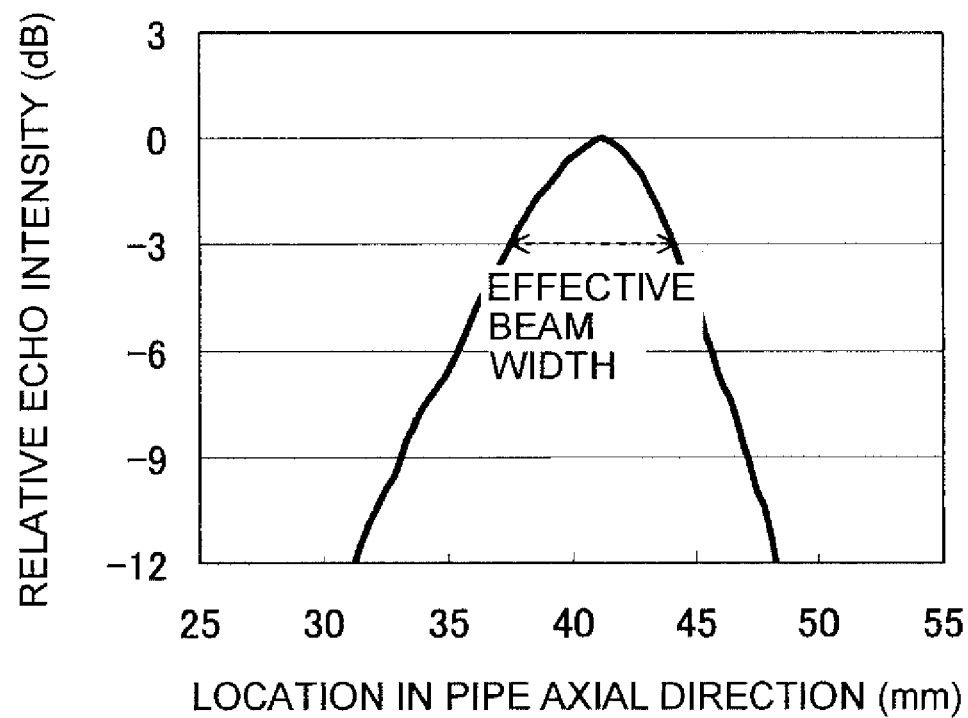

FIG. 6A and 6B give profile examples of echo intensity from a target flaw (circumferential flaw) that is obtained when one selected transducer group that transmit and receive ultrasonic waves substantially at the same time is scanned along the arrangement direction of the transducers. In FIGS. 6A and 6B, the abscissa represents the value obtained by converting the scanning location of the selected transducer group into a location in the axial direction of pipe. FIG. 6A shows the profile of echo intensity from a circumferential flaw (depth: 5% of wall thickness, circumferential length: 25 mm) produced on the pipe P having an outside diameter of 178 mm and a wall thickness of 10 mm. FIG. 6B shows the profile of echo intensity from a circumferential flaw (depth: 5% of wall thickness, circumferential length: 25 mm) produced on the pipe P having an outside diameter of 160 mm and a wall thickness of 20 mm. It is found that, if the range in which the echo intensity is −3 dB or higher when the highest intensity is set at 0 dB is an effective beam width W1, the W1 in the example shown in FIG. 6A is approximately equal to 9.5 mm, and the W1 in the example shown in FIG. 6B is approximately equal to 6.75 mm.

Since $\theta=\alpha\approx 19°$, substitution of this value of $\theta$ and the aforementioned value of W1 into formula (1) gives $$P \leq 9.5 \times \cos 19° = 9.5 \times 0.95 = 8.98 \text{ mm}$$

for the pipe P having an outside diameter of 178 mm and a wall thickness of 10 mm, and $$P \leq 6.75 \times \cos 19° = 6.75 \times 0.95 = 6.38 \text{ mm}$$

for the pipe P having an outside diameter of 160 mm and a wall thickness of 20 mm.

In this embodiment, as described above, since 64 transducers 11 included in the ultrasonic probe 1 are arranged at an equal arrangement pitch of d=0.5 (mm), substitution of the values of $\theta$, W1 and d into formula (2) gives $$K \leq 9.5 \times \cos 19°/0.5 = 9.5 \times 0.95/0.5 = 17.96$$

for the pipe P having an outside diameter of 178 mm and a wall thickness of 10 mm, so that it is easily found that transducer group to be selected have only to be switched successively by the switching pitch number of 17 or smaller.

Also, $$K 6.75 \times \cos 19°/0.5 = 6.75 \times 0.95/0.5 = 12.76$$

for the pipe P having an outside diameter of 160 mm and a wall thickness of 20 mm, so that it is easily found that transducer group to be selected have only to be switched successively by the switching pitch number of 12 or smaller.

The control section 23 operates so as to determine the delay time set by the delay circuit 212 or the delay circuit 222 for each of the transducers 11 constituting the transducer group. In this embodiment, since ultrasonic waves are transmitted and received substantially at the same time from/by the transducers 11 constituting the transducer group, the same transmission delay time and reception delay time are set for transducers 11.

Also, the control section 23 operates so as to change the amplification degree (testing sensitivity) of the amplifier 224 for each selected transducer group. Specifically, the amplification degree of the amplifier 224 is capable of being changed, and the control section 23 sends a control signal for changing the amplification degree according to the selected transducer group to the amplifier 224 so that the amplification degree determined beforehand for each selected transducer group is provided. As described above, the amplification degree of each selected transducer group is determined beforehand so that the highest echo intensities from target flaws received by each selected transducer group are approximately equivalent.

The ultrasonic testing apparatus 100 in accordance with this embodiment performs ultrasonic testing, following the testing cycle described below, for example, while rotating the pipe P having an outside diameter of 178 mm and a wall thickness of 10 mm, for example, in the circumferential direction by using the driving device and relatively moving the ultrasonic probe 1 in the axial direction of the pipe P. The control section 23 of this embodiment switches transducer group to be selected by shifting the transducers 11 to be selected by 17 pieces at a time (i.e., the switching pitch number for the transducer group to be selected is 17) as shown in the testing cycle described below.

<Testing Cycle>

(1) Step 1: Ultrasonic testing is performed using a transducer group consisting of transducers 11-1 to 11-30.

(2) Step 2: Ultrasonic testing is performed using a transducer group consisting of transducers 11-18 to 11-47.

(3) Step 3: Ultrasonic testing is performed using a transducer group consisting of transducers 11-35 to 11-64.

By repeating the above-described steps 1 to 3, the whole of the pipe P is tested ultrasonically.

As described above, specifically, the amplification degree of the amplifier 224 changed for each selected transducer group is determined beforehand as described below. The amplification degree of the amplifier 224 is determined so that the highest echo intensity from the circumferential flaw that is obtained when ultrasonic waves are transmitted and received by the transducers group consisting of the transducers 11-1 to 11-30 selected in step 1 is a predetermined intensity (for example, intensity of 80% on the CRT). Also, the amplification degree of the amplifier 224 is determined so that the highest echo intensity from the circumferential flaw that is obtained when ultrasonic waves are transmitted and received by the transducers group consisting of the transducers 11-18 to 11-47 selected in step 2 is an intensity approximately equivalent to the aforementioned value (for example, intensity of 80% on the CRT). Further, the amplification degree of the amplifier 224 is determined so that the highest echo intensity from the circumferential flaw that is obtained when ultrasonic waves are transmitted and received by the transducers group consisting of the transducers 11-35 to 11-64 selected in step 3 is an intensity approximately equivalent to the aforementioned value (for example, intensity of 80% on the CRT). By doing this, the amplification degree of the amplifier 224 changed for each selected transducer group is determined beforehand, and the control section 23 also changes the amplification degree of the amplifier 224 according to the selected transducer group so that the amplification degree determined beforehand for each selected transducer group is provided.

Figure 7:
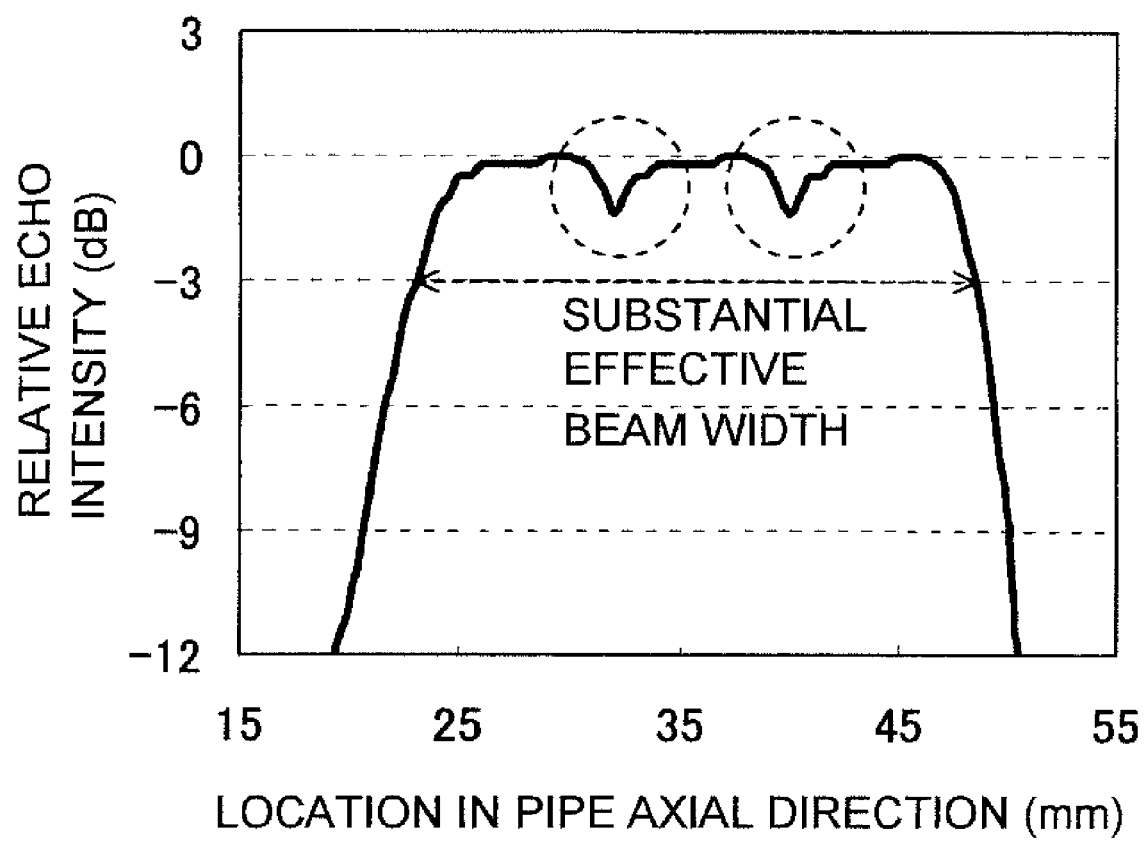
FIG. 7 is a diagram showing an example in which the profiles of echo intensity from a target flaw that is obtained for each selected m number of transducers included in the ultrasonic probe shown in FIGS. 5A and 5B are combined.

FIG. 7 is a diagram showing an example in which the profiles of echo intensity from a target flaw (circumferential flaw) that is obtained for each transducer group selected in each of the above-described steps are combined. As shown in FIG. 7, the combined profile of flaw echo intensity has a portion in which the echo intensity is high over a wide range in the axial direction of pipe as compared with the profile of flaw echo intensity obtained for one selected transducer group (for one step) shown in FIG. 6A. In the combined profile of flaw echo intensity shown in FIG. 7, if a range in which the echo intensity is −3 dB or higher when the highest intensity is set at 0 dB is a substantial effective beam width, the substantial effective beam width is about 25 mm. Also, from FIG. 7, it is revealed that the decrease in flaw echo intensity in the boundary portion (a portion encircled by a broken line in FIG. 7) of each selected transducer group can be kept to about −1.5 dB.

As described above, according to the ultrasonic testing apparatus 100 in accordance with this embodiment, since the substantial effective beam width is wide, even if a target flaw is present at any location within the testing region of the ultrasonic probe 1, the target flaw is located within the range of effective beam width of any selected transducer group. Therefore, flaw echo intensity not lower than the predetermined intensity (−3 dB when the maximum value of flaw echo intensity obtained by the ultrasonic probe 1 is set at 0 dB) can be provided, so that a target flaw can be detected with high accuracy.

<Second Embodiment>

Figure 8C:
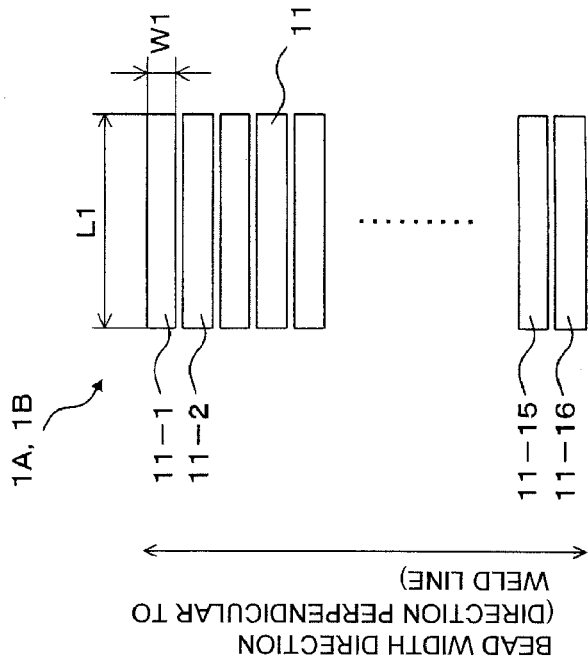
FIGS. 8A to 8C give schematic views showing a schematic configuration of an ultrasonic testing apparatus in accordance with a second embodiment of the present invention.
Figure 8A:
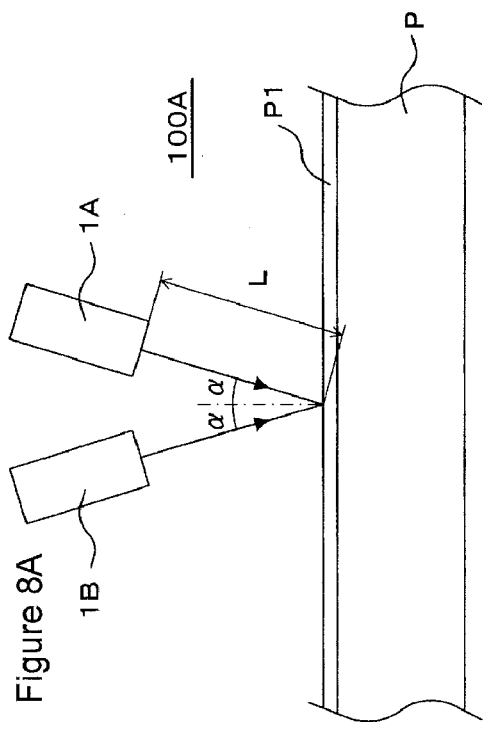
Figure 8B:
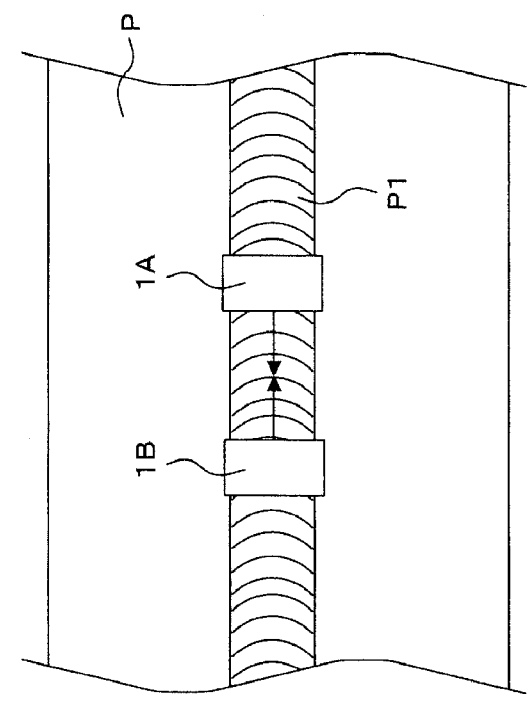

FIGS. 8A to 8C give schematic views showing a schematic configuration of an ultrasonic testing apparatus in accordance with a second embodiment of the present invention, FIG. 8A being a front view, FIG. 8B being a plan view, and FIG. 8C being an enlarged plan view of an ultrasonic probe (an enlarged plan view in a state in which the ultrasonic probe is not tilted).

An ultrasonic testing apparatus 100A in accordance with this embodiment is an ultrasonic testing apparatus for detecting flaws present in welded portions. As shown in FIG. 8, the ultrasonic testing apparatus 100A in accordance with this embodiment comprises ultrasonic probes 1A and 1B including 16 transducers 11 (11-1 to 11-16) arranged along the direction perpendicular to the weld line of a welded portion P1 of a pipe P, disposed so as to face the welded portion P1. Also, the ultrasonic testing apparatus 100A in accordance with this embodiment comprises a transmission/reception control device 2 (not shown) for selecting 10 transducers 11 (in this embodiment, a set of 10 transducers 11 is called transducer group) from among the 16 transducers 11, transmitting ultrasonic waves from the selected transducer group toward the welded portion P1, receiving the ultrasonic waves therefrom, and switching transducer group to be selected successively. Also, the ultrasonic testing apparatus 100A in accordance with this embodiment includes a flaw evaluation section 3 (not shown) that detects a flaw present in the pipe P by comparing the output signal sent from the transmission/reception control device 2 with a predetermined threshold value. Further, the ultrasonic testing apparatus 100A in accordance with this embodiment comprises a driving device (not shown) for moving the ultrasonic probes 1A and 1B relatively to the pipe P in the direction of the weld line of the welded portion P1.

The ultrasonic testing apparatus 100A in accordance with this embodiment comprises a pair of ultrasonic probes 1A and 1B as a preferred configuration for evaluating acoustic coupling of the ultrasonic probe with the pipe P as described later. The pair of ultrasonic probes 1A and 1B are disposed substantially in a V shape so that ultrasonic waves transmitted from the transducers 11 included in each of the ultrasonic probes 1A and 1B enter the approximately identical point in the welded portion P1 as viewed from the direction perpendicular to the weld line of the welded portion P1, and that the echoes reflected from the surface of the welded portion P1 of the ultrasonic waves transmitted from the transducers 11 included in one ultrasonic probe 1A can be received by the transducers 11 included in the other ultrasonic probe 1B.

The ultrasonic probes 1A and 1B of this embodiment are disposed separated from the pipe P by a distance of L=70 mm. Also, the ultrasonic probes 1A and 1B are disposed tilted by an angle of α19° in the weld line direction from the normal to the surface of the pipe P (so that the angle of incidence a of ultrasonic wave is approximately equal to) 19°. Thereby, ultrasonic shear waves having an angle of refraction of 45° are propagated along the weld line direction. The testing frequencies of the ultrasonic probes 1A and 1B of this embodiment are set at 5 MHz.

Each of the transducers 11 included in each of the ultrasonic probes 1A and 1B of this embodiment is a transducer having the same rectangular shape, and the transducers 11 are arranged in a straight line in the direction perpendicular to the weld line of the welded portion P1 (the bead width direction). Each of the transducers 11 of this embodiment has a length of L1=10 mm and a width of W1=0.9 mm, and the transducers 11 are arranged with a gap of 0.1 mm being provided therebetween. This means that the arrangement pitch for the transducers 11 in the direction perpendicular to the weld line is 1.0 mm. The ultrasonic probes 1A and 1B are disposed so that the transducers 11-8 and 11-9 are opposed to the center in the bead width direction of the welded portion P1.

The transmission/reception control device 2 of this embodiment has the same configuration as that of the transmission/reception control device 2 of the first embodiment, and therefore the detailed explanation thereof is omitted. Like the transmission/reception control device 2 of the first embodiment, the transmission/reception control device 2 of this embodiment comprises a transmission section 21, a reception section 22, and a control section 23. The reception section 22 includes an amplifier 224. However, the ultrasonic testing apparatus 100A in accordance with this embodiment comprises the transmission/reception control device 2 connected to one ultrasonic probe 1A and the transmission/reception control device 2 connected to the other ultrasonic probe 1B. Like the control section 23 of the first embodiment, the control section 23 of this embodiment successively switches transducer group to be selected by the switching pitch length P (mm) satisfying the aforementioned formula (1). In particular, in the case where the 16 transducers 11 included in the ultrasonic probes 1A and 1B are arranged at an equal arrangement pitch as in this embodiment, the control section 23 successively switches transducer group to be selected by the switching pitch number K, satisfying the aforementioned formula (2).

FIG. 9 gives a profile example of echo intensity of a target flaw (a vertical hole having an inside diameter of 1.6 mm) that is obtained when one selected transducer group that transmit and receive ultrasonic waves substantially at the same time is scanned along the arrangement direction of the transducers (the bead width direction). It is found that, if the range in which the echo intensity is −3 dB or higher when the highest intensity is set at 0 dB is an effective beam width W1, the W1 in the example shown in FIG. 9 is approximately equal to 3.8 mm.

In this embodiment, since it can be thought that an angle θ that the arrangement direction of transducers 11 (the bead width direction) makes with the surface of the pipe P which ultrasonic wave enters (the tangential plane of the pipe P at the incident point of ultrasonic wave) is 0°, substitution of this value of θ and the aforementioned value of W1 into the aforementioned formula (1) gives $$P \leq 3.8 \times \cos 0° = 3.8 \times 1 = 3.8 \text{ mm.}$$

In this embodiment, since 16 transducers 11 included in the ultrasonic probes 1A and 1B are arranged at an equal arrangement pitch of d=1.0 (mm), substitution of the values of θ, W1 and d into the aforementioned formula (2) gives $$K \leq 3.8 \times \cos 0°/1.0 = 3.8 \times 1/1.0 = 3.8$$

so that it is easily found that transducer group to be selected have only to be switched successively by the switching pitch number of 3 or smaller.

From this finding, the ultrasonic testing apparatus 100A in accordance with this embodiment performs ultrasonic testing, following the testing cycle described below, for example, while moving the ultrasonic probe 1 relatively to the pipe P in the direction of the weld line of the welded portion P1. The control section 23 of this embodiment switches transducer group to be selected by shifting the transducers 11 to be selected by 3 pieces at a time (i.e., the switching pitch number for the transducer group to be selected is 3) as shown in the testing cycle described below.

<Testing Cycle>

(1) Step 1: Ultrasonic testing is performed using a transducer group consisting of transducers 11-1 to 11-10.

(2) Step 2: Ultrasonic testing is performed using a transducer group consisting of transducers 11-4 to 11-13.

(3) Step 3: Ultrasonic testing is performed using a transducer group consisting of transducers 11-7 to 11-16.

By repeating the above-described steps 1 to 3, the whole of the pipe P is tested ultrasonically.

The amplification degree (testing sensitivity) of the amplifier 224 changed for each selected transducer group is determined beforehand as described below. The amplification degree of the amplifier 224 is determined so that the highest echo intensity from a vertical hole C (a vertical hole having an inside diameter of 1.6 mm produced at a location −5 mm away from the center in the bead width direction of the welded portion) shown in FIG. 10A that is obtained when ultrasonic waves are transmitted and received by the transducer group consisting of the transducers 11-1 to 11-10 selected in step 1 is a predetermined intensity (for example, an intensity of 80% on the CRT). Also, the amplification degree of the amplifier 224 is determined so that the highest echo intensity from a vertical hole B (a vertical hole having an inside diameter of 1.6 mm produced at a location at the center in the bead width direction of the welded portion) shown in FIG. 10A that is obtained when ultrasonic waves are transmitted and received by the transducer group consisting of transducers 11-4 to 11-13 selected in step 2 is an intensity approximately equivalent to the aforementioned value (for example, an intensity of 80% on the CRT). Further, the amplification degree of the amplifier 224 is determined so that the highest echo intensity from a vertical hole A (a vertical hole having an inside diameter of 1.6 mm produced at a location +5 mm away from the center in the bead width direction of the welded portion) shown in FIG. 10A that is obtained when ultrasonic waves are transmitted and received by the transducer group consisting of transducers 11-7 to 11-16 selected in step 3 is an intensity approximately equivalent to the aforementioned value (for example, an intensity of 80% on the CRT). In this manner, the amplification degree of the amplifier 224 changed for each selected transducer group is determined beforehand, and the control section 23 also changes the amplification degree of the amplifier 224 according to the selected transducer group so that the amplification degree determined beforehand for each selected transducer group is provided.

In this embodiment, as a preferred configuration, acoustic coupling of the ultrasonic probes 1A and 1B with the steel pipe P is evaluated after a series of ultrasonic testing of the welded portion P1 using all selected transducer group successively (aforementioned steps 1 to 3) is finished, and before the next series of ultrasonic testing is started. Specifically, ultrasonic waves are transmitted from the transducers 11-4 to 11-13 included in one ultrasonic probe 1A, and the echoes reflected from the surface of the welded portion P1 of the transmitted ultrasonic waves are received by the transducers 11-4 to 11-13 included in the other ultrasonic probe 1B, whereby the magnitude of echo intensity is evaluated. The above-described operation is controlled by overall control means (not shown) that controls both of the transmission/reception control device 2 connected to one ultrasonic probe 1A and the transmission/reception control device 2 connected to the other ultrasonic probe 1B. And, if the intensity of echo reflected from the surface of the welded portion P1 is not higher than a predetermined level, an alarm is given by the overall control means. With such a configuration, after adjustment has been made so that the acoustic coupling is normal, a measure for retesting can be taken, and the flaw detection accuracy can be stabilized.

Figure 10A:
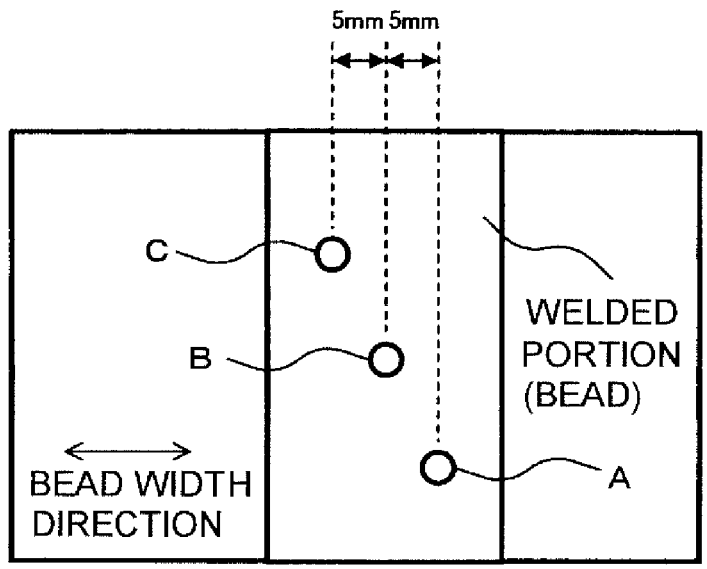
FIGS. 10A and 10B give diagrams showing one example of a result of ultrasonic testing performed by using the ultrasonic testing apparatus shown in FIGS. 8A to 8C.
Figure 10B:
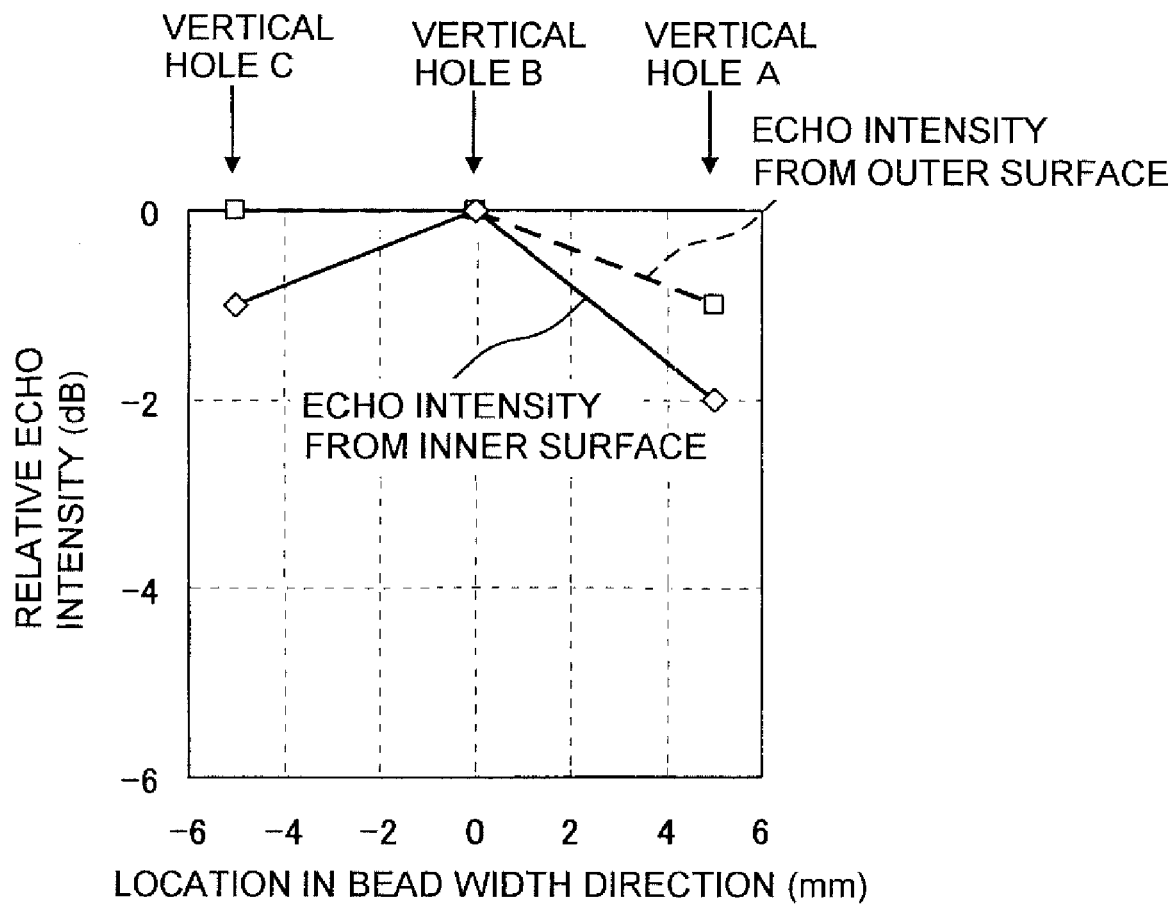

FIG. 10B is a graph showing a result of ultrasonic testing of the vertical holes A to C shown in FIG. 10A performed by using the ultrasonic testing apparatus 100A having the configuration explained above. The abscissa in FIG. 10B represents the location in the bead width direction, and the ordinate represents the highest echo intensities on the inner and outer surfaces of each of the vertical holes, which are outputted from a waveform synthesis circuit 223 included in the reception section 22.

As can be seen from FIG. 10B, according to the ultrasonic testing apparatus 100A in accordance with this embodiment, a flaw in the inner and outer surfaces can be detected accurately regardless of the location at which the flaw is present (the location in the bead width direction).

<Third Embodiment>

Figure 11A:
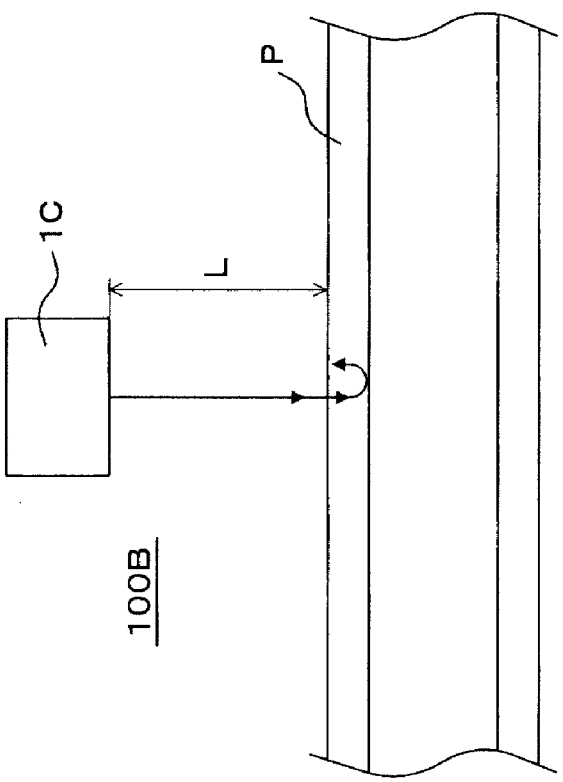
FIGS. 11A and 11B give schematic views showing a schematic configuration of an ultrasonic testing apparatus in accordance with a third embodiment of the present invention.
Figure 11B:
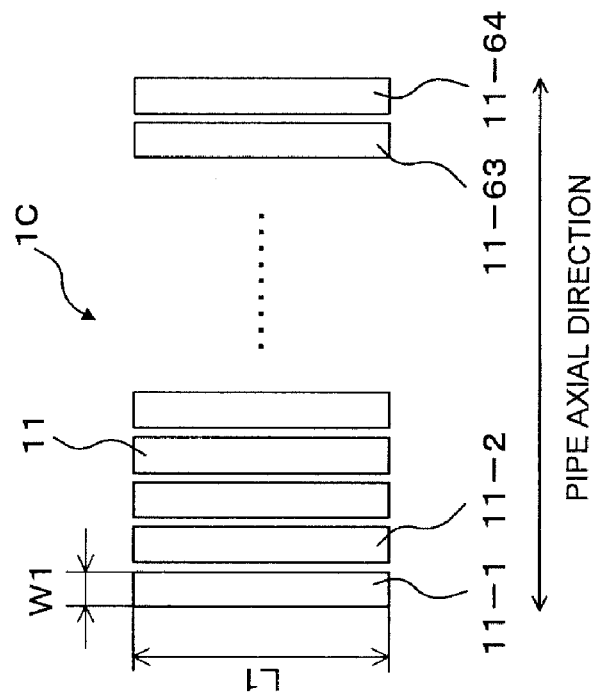

FIG. 11A and 11B give schematic views showing a schematic configuration of an ultrasonic testing apparatus in accordance with a first embodiment of the present invention, FIG. 11A being a front view (a sectional view of the pipe), and FIG. 11B being an enlarged plan view of an ultrasonic probe shown in FIG. 11A (an enlarged plan view in a state in which the ultrasonic probe is not tilted).

An ultrasonic testing apparatus 100B in accordance with this embodiment is an ultrasonic testing apparatus for detecting a lamination. As shown in FIGS. 11A and 11B, the ultrasonic testing apparatus 100B in accordance with this embodiment comprises an ultrasonic probe 1C including 64 transducers 11 (11-1 to 11-64) arranged along the axial direction of a pipe P, disposed so as to face the pipe P. Also, the ultrasonic testing apparatus 100B in accordance with this embodiment comprises a transmission/reception control device 2 (not shown) for selecting 36 transducers 11 (in this embodiment, a set of 36 transducers 11 is called transducer group) from among the 64 transducers 11, transmitting ultrasonic waves from the selected transducer group toward the pipe P, receiving the ultrasonic waves therefrom, and switching transducer group to be selected successively. Also, the ultrasonic testing apparatus 100B in accordance with this embodiment comprises a flaw evaluation section 3 (not shown) that detects a flaw present in the pipe P by comparing the output signal sent from the transmission/reception control device 2 with a predetermined threshold value. Further, the ultrasonic testing apparatus 100B in accordance with this embodiment comprises a driving device (not shown) for rotating the pipe P in the circumferential direction and relatively moving the ultrasonic probe 1C in the axial direction of the pipe P.

The ultrasonic probe 1C of this embodiment is disposed separated from the pipe P by a distance of L=70 mm. Also, the ultrasonic probe 1C is disposed so that the transmitted ultrasonic waves enter the surface of the pipe P perpendicularly. Thereby, ultrasonic longitudinal waves are propagated in the wall thickness direction of the pipe P. The testing frequency of the ultrasonic probe 1C of this embodiment is set at 7 MHz.

Each of the transducers 11 included in the ultrasonic probe 1C of this embodiment is a transducer having the same rectangular shape, and the transducers 11 are arranged in a straight line in the axial direction of the pipe P. Each of the transducers 11 of this embodiment has a length of L1=10 mm and a width of W1=0.4 mm, and the transducers 11 are arranged with a gap of 0.1 mm being provided therebetween. This means that the arrangement pitch for the transducers 11 in the axial direction of the pipe P is 0.5 mm.

The transmission/reception control device 2 of this embodiment has the same configuration as that of the transmission/reception control device 2 of the first embodiment, and therefore the detailed explanation thereof is omitted. Like the transmission/reception control device 2 of the first embodiment, the transmission/reception control device 2 of this embodiment comprises a transmission section 21, a reception section 22, and a control section 23. The reception section 22 includes an amplifier 224. Like the control section 23 of the first embodiment, the control section 23 of this embodiment successively switches transducer group by the switching pitch length P (mm) satisfying the aforementioned formula (1). In particular, in the case where the 64 transducers 11 included in the ultrasonic probe 1C are arranged at an equal arrangement pitch as in this embodiment, the control section 23 successively switches transducer group to be selected by the switching pitch number K, satisfying the aforementioned formula (2).

Figure 12A:
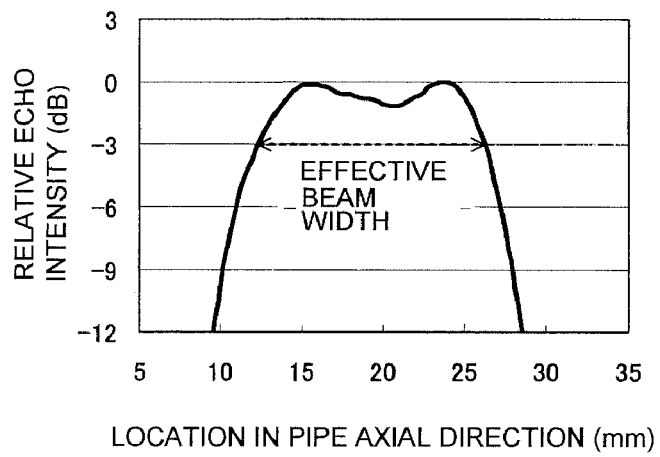
FIGS. 12A and 12B give diagrams showing a profile example of echo intensity from a target flaw that is obtained when selected m number of transducers included in the ultrasonic probe shown in FIGS. 11A and 11B are scanned along the arrangement direction of thereof, and an example in which the profiles of echo intensity from a target flaw that is obtained for each selected m number of transducers are combined.

FIG. 12A gives a profile example of echo intensity of a target flaw (a flat-bottom hole having an inside diameter of 6.35 mm simulating lamination, which is produced at the inner surface of the pipe P) that is obtained when one selected transducer group that transmit and receive ultrasonic waves substantially at the same time is scanned along the arrangement direction thereof (the axial direction of the pipe P). It is found that, if the range in which the echo intensity is −3 dB or higher when the highest intensity is set at 0 dB is an effective beam width W1, the W1 in the example shown in FIG. 12A is approximately equal to 13.75 mm.

In this embodiment, since it can be thought that an angle θ that the arrangement direction of transducers 11 (the axial direction of the pipe P) makes with the surface of the pipe P which ultrasonic wave enters (the tangential plane of the pipe P at the incident point of ultrasonic wave) is 0°, substitution of this value of θ and the aforementioned value of W1 into the aforementioned formula (1) gives $$P \leqq 13.75 \times \cos 0° = 13.75 \times 1 = 13.75 \text{ mm.}$$

In this embodiment, since 64 transducers 11 included in the ultrasonic probe 1C are arranged at an equal arrangement pitch of d=0.5 (mm), substitution of the values of θ, W1 and d into the aforementioned formula (2) gives $$K \leqq 13.75 \times \cos 0°/0.5 = 13.75 \times 1/0.5 = 27.5$$

so that it is easily found that transducer group to be selected have only to be switched successively by the switching pitch number of 27 or smaller.

From this finding, the ultrasonic testing apparatus 100B in accordance with this embodiment performs ultrasonic testing, following the testing cycle described below, for example, while rotating the pipe P in the circumferential direction by the driving device and relatively moving the ultrasonic probe 1C in the axial direction of the pipe P. The control section 23 of this embodiment switches transducer group to be selected by shifting the transducers 11 to be selected by 27 pieces at a time (i.e., the switching pitch number for the transducer group to be selected is 27) as shown in the testing cycle described below.

<Testing Cycle>

(1) Step 1: Ultrasonic testing is performed using a transducer group consisting of transducers 11-1 to 11-36.

(2) Step 2: Ultrasonic testing is performed using a transducer group consisting of transducers 11-28 to 11-63.

By repeating the above-described steps 1 and 2, the whole of the pipe P is tested ultrasonically.

The amplification degree (testing sensitivity) of the amplifier 224 changed for each selected transducer group is determined beforehand as described below. The amplification degree of the amplifier 224 is determined so that the highest echo intensity from the flat-bottom hole that is obtained when ultrasonic waves are transmitted and received by the transducer group consisting of the transducers 11-1 to 11-36 selected in step 1 is a predetermined intensity (for example, an intensity of 80% on the CRT). Also, the amplification degree of the amplifier 224 is determined so that the highest echo intensity from the flat-bottom that is obtained when ultrasonic waves are transmitted and received by the transducer group consisting of the transducers 11-28 to 11-63 selected in step 2 is an intensity approximately equivalent to the aforementioned value (for example, an intensity of 80% on the CRT). In this manner, the amplification degree of the amplifier 224 changed for each selected transducer group is determined beforehand, and the control section 23 also changes the amplification degree of the amplifier 224 according to the selected transducer group so that the amplification degree determined beforehand for each selected transducer group is provided.

Figure 12B:
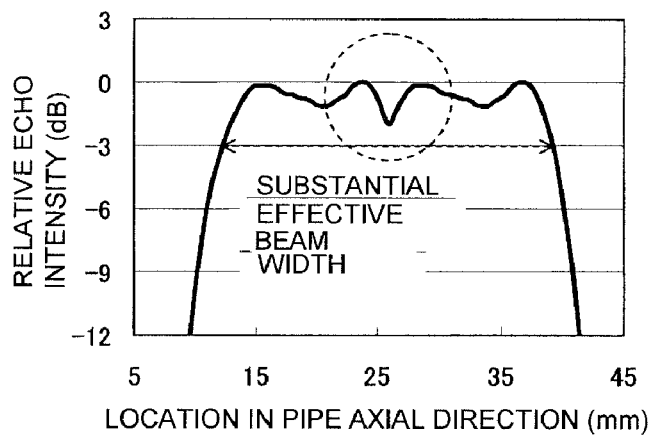

FIG. 12B is a diagram showing an example in which the profiles of echo intensity from a target flaw (flat-bottom hole) that is obtained for each transducer group selected in each of the above-described steps are combined. As shown in FIG. 12B, the combined profile of flaw echo intensity has a portion in which the echo intensity is high over a wide range in the axial direction of pipe as compared with the profile of flaw echo intensity obtained for one selected transducer group (for one step) shown in FIG. 12A. In the combined profile of flaw echo intensity shown in FIG. 12B, if a range in which the echo intensity is −3 dB or higher when the highest intensity is set at 0 dB is a substantial effective beam width, the substantial effective beam width is about 27.25 mm. Also, from FIG. 12B, it is revealed that the decrease in flaw echo intensity in the boundary portion (a portion encircled by a broken line in FIG. 12B) of each selected transducer group can be kept to about −2 dB.

As described above, according to the ultrasonic testing apparatus 100B in accordance with this embodiment, since the substantial effective beam width is wide, even if a target flaw is present at any location within the testing region of the ultrasonic probe 1C, the target flaw is located within the range of effective beam width of any selected transducer group. Therefore, flaw echo intensity not lower than the predetermined intensity (−3 dB when the maximum value of flaw echo intensity obtained by the ultrasonic probe 1C is set at 0 dB) can be provided, so that a target flaw can be detected with high accuracy.

In the first to third embodiments described above, explanation has been given about the configuration in which the ultrasonic probes 1, 1A to 1C includes the plurality of transducers 11 having the same shape arranged in a straight line at the equal arrangement pitch. However, the present invention is not limited to this configuration, and for example, an ultrasonic probe including a plurality of transducers 11A and 11B having nonuniform widths (the widths of the transducer 11A and the transducer 11B are different) arranged in a straight line as shown in FIG. 13 or an ultrasonic probe including a plurality of transducers arranged in a zigzag form may also be used.

Figure 13A:
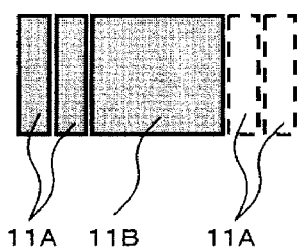
FIG. 13 is a schematic view showing a modified example of a transducer included in the ultrasonic probe used in the present invention.
Figure 13B:
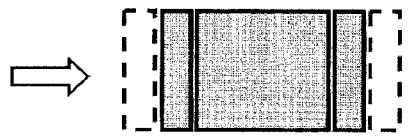
Figure 13C:
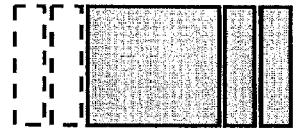

However, even in the case where the ultrasonic probe as shown in FIG. 13 or the ultrasonic probe including a plurality of transducers arranged in a zigzag form is used, as in the case where the ultrasonic probes 1, 1A to 1C of the first to third embodiments is used, it is necessary to successively switch transducer group to be selected by the switching pitch length P (mm) satisfying the aforementioned formula (1). In the example shown in FIG. 13, when shaded transducer group is selected successively from step 1 to step 3, the switching pitch length P represented by a distance between the transducer group selected in step 1 and the transducer group selected in step 2 and the switching pitch length P represented by a distance between the transducer group selected in step 2 and the transducer group selected in step 3 must satisfy the aforementioned formula (1). Also, it is necessary to adjust the testing sensitivity beforehand for each selected transducer group so that the highest echo intensities from target flaws received by each selected transducer group are approximately equivalent.

<Fourth Embodiment>

Figure 14C:
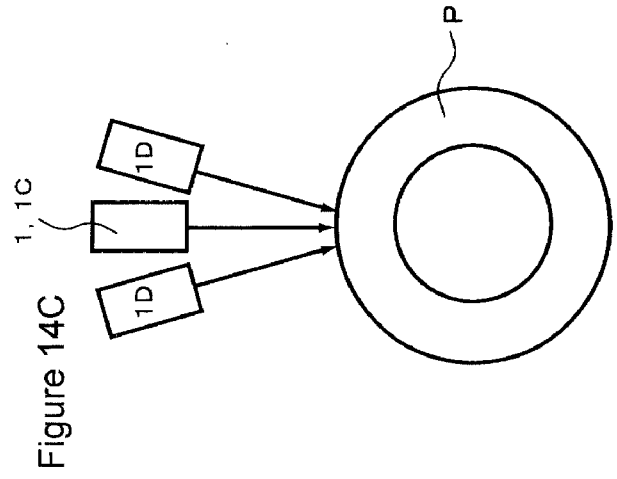
FIGS. 14A to 14C give schematic views showing a schematic configuration of an ultrasonic testing apparatus in accordance with a fourth embodiment of the present invention.
Figure 14A:
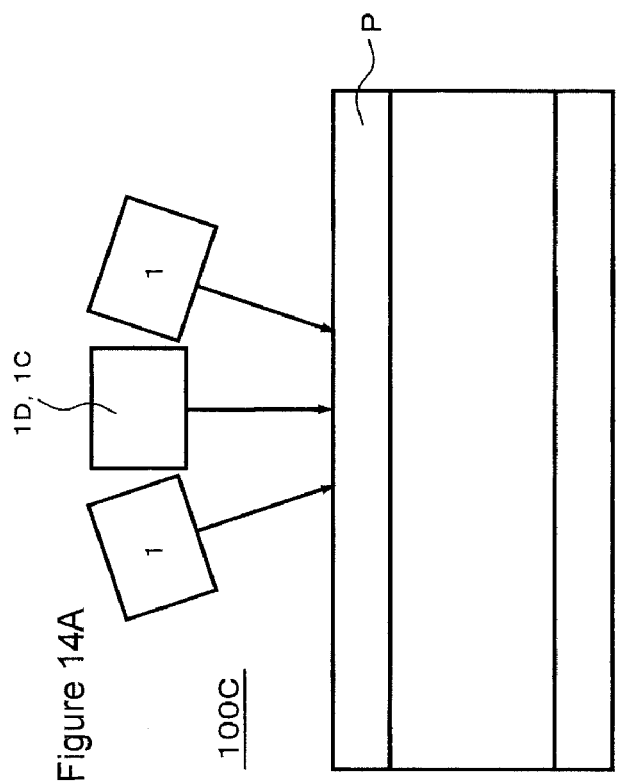
Figure 14B:
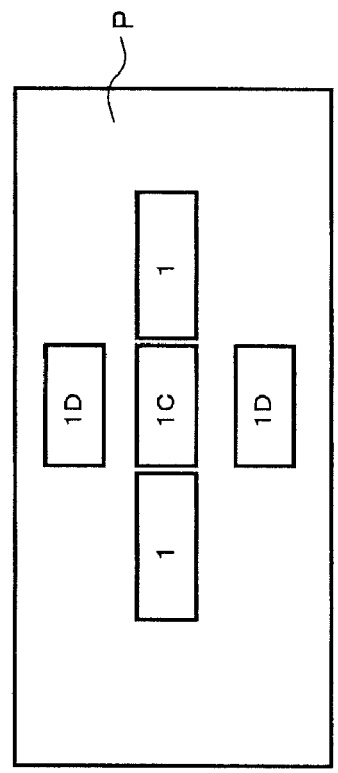

FIGS. 14A to 14C give schematic views showing a schematic configuration of an ultrasonic testing apparatus in accordance with a fourth embodiment of the present invention, FIG. 14A being a front view (a sectional view for a pipe), FIG. 14B being a plan view, and FIG. 14C being a side view.

As shown in FIGS. 14 A to 14C, an ultrasonic testing apparatus 100C in accordance with this embodiment comprises two ultrasonic probes 1 for detecting circumferential flaws having the same configuration as that of the above-described first embodiment, one ultrasonic probe 1C for detecting lamination having the same configuration as that of the above-described third embodiment, and two ultrasonic probes 1D for detecting axial flaws having a single transducer.

Also, the ultrasonic testing apparatus 100C includes a transmission/reception control device (not shown) connected to the ultrasonic probes 1, 1C and 1D. The transmission/reception control device connected to the ultrasonic probes 1 and 1C have the same configuration as that of the transmission/reception control device 2 of the above-described first and third embodiments, and perform functions of transmitting ultrasonic waves from the selected transducer group toward a pipe P, receiving the ultrasonic waves therefrom, and successively switching transducer group to be selected. The transmission/reception control device connected to the ultrasonic probe 1D performs a function of transmitting ultrasonic waves from the single transducer included in the ultrasonic probe 1D toward the pipe P, and receiving the ultrasonic waves therefrom.

Further, the ultrasonic testing apparatus 100C comprises a flaw evaluation section (not shown) that detects a flaw present in the pipe P by comparing the output signal sent from the transmission/reception control device with a predetermined threshold value, and a driving device (not shown) for rotating the pipe P in the circumferential direction and relatively moving the ultrasonic probes 1, 1C and 1D in the axial direction of the pipe P.

The driving device of this embodiment has a feature of rotating the pipe P in the circumferential direction and relatively moving the ultrasonic probes 1, 1C and 1D in the axial direction of the pipe P so that the amount of relative displacement in the axial direction of the pipe P of the ultrasonic probes 1, 1C, 1D per one turn of the pipe P is not larger than the minimum substantial effective beam width of the substantial effective beam widths of the ultrasonic probes 1, 1C and 1D in the axial direction of the pipe P for a target flaw. Specific explanation of this feature is given below.

For the ultrasonic probe 1, the substantial effective beam width in the axial direction of the pipe P is about 25 mm as described in the first embodiment. For the ultrasonic probe 1C, the substantial effective beam width in the axial direction of the pipe P is about 27.25 mm as described in the third embodiment. For the ultrasonic probe 1D, though the detailed description is omitted, by setting the length along the axial direction of the pipe P of the single transducer included in the ultrasonic probe 1D at a proper value, the substantial effective beam width in the axial direction of the pipe P for a target flaw (an axial flaw) can be increased to about 20 mm.

Therefore, the driving device of this embodiment rotates the pipe P in the circumferential direction and relatively moves the ultrasonic probes 1, 1C and 1D in the axial direction of the pipe P so that the amount of relative displacement in the axial direction of the pipe P of the ultrasonic probes 1, 1C, 1D per one turn of the pipe P is not larger than the minimum substantial effective beam width of the substantial effective beam widths of the ultrasonic probes 1, 1C and 1D in the axial direction of the pipe P for a target flaw, that is, not larger than about 20 mm. The relative movement of the ultrasonic probes 1, 1C and 1D in the axial direction of the pipe P may be performed with the ultrasonic probes 1, 1C and 1D being at standstill and the pipe P being moved in the axial direction, or may be performed with the pipe P being at standstill and the ultrasonic probes 1, 1C and 1D being moved in the axial direction of the pipe P.

According to the ultrasonic testing apparatus 100C in accordance with this embodiment, even if a target flaw is present in any portion of the pipe P, for all of the ultrasonic probes 1, 1C and 1D, the echo intensity of the target flaw is not lower than a predetermined intensity, and as a result of this, all of axial flaw, circumferential flaw, and lamination can be detected with high accuracy.

The invention claimed is:

1. An ultrasonic testing method, comprising:
a disposing step of disposing an ultrasonic probe including n (n≧2) number of transducers arranged along a predetermined direction so as to face a test object;
a testing step of testing the test object by selecting m (n>m≧1) number of transducers from among the n number of transducers, transmitting ultrasonic waves from the selected m number of transducers toward the test object and receiving the ultrasonic waves therefrom; and
a scanning step of switching m number of transducers to be selected successively,
the method repeating the testing step and the scanning step alternately, thereby ultrasonic testing the test object,
wherein, in the scanning step, if an angle that the arrangement direction of the n number of transducers makes with the surface of the test object which ultrasonic waves enter is θ(°), and the effective beam width of each selected m number of transducers with respect to a target flaw is W1 (mm), m number of transducers to be selected are switched successively by a switching pitch length P (mm) satisfying the following formula (1):

$$P \leq W1 \cdot \cos \theta \quad (1)$$

and, in the testing step, the test object is tested with testing sensitivity adjusted beforehand for each selected m number of transducers so that the highest echo intensities from target flaws received by each selected m number of transducers are approximately equivalent.

2. The ultrasonic testing method according to claim 1, wherein the n number of transducers included in the ultrasonic probe are arranged at an equal arrangement pitch of d (mm), and in the scanning step, if an angle that the arrangement direction of the n number of transducers makes with the surface of the test object which ultrasonic waves enter is θ(°), and the effective beam width of each selected m number of transducers with respect to a target flaw is W1 (mm), m number of transducers to be selected are switched successively by a switching pitch number K satisfying the following formula (2):

$$K \leq W1 \cdot \cos \theta / d \qquad (2).$$

3. An ultrasonic testing method,
the method disposing a first ultrasonic probe for detecting an axial flaw which is possible to occur in a pipe or tube as a test object, a second ultrasonic probe for detecting a circumferential flaw which is possible to occur in the pipe or tube, and a third ultrasonic probe for detecting a lamination which is possible to occur in the pipe or tube, so as to face the pipe or tube, and
while rotating the pipe or tube in the circumferential direction and relatively moving the first to third ultrasonic probes in the axial direction of the pipe or tube, transmitting ultrasonic waves from transducers included in the first to third ultrasonic probes toward the pipe or tube and receiving the ultrasonic waves therefrom, thereby ultrasonic testing the pipe or tube,
wherein at least one ultrasonic probe selected from among the first to third ultrasonic probes is an ultrasonic probe including n (n≧2) number of transducers arranged along a predetermined direction so as to face a test object, the arrangement direction of n number of transducers included in the selected ultrasonic probe is aligned with the axial direction of the pipe or tube, and the ultrasonic testing method according to claim 1 is carried out for the selected ultrasonic probe, and
wherein the amount of relative displacement in the axial direction of the pipe or tube of the first to third ultrasonic probes per one turn of the pipe or tube is set so as to be not larger than the minimum substantial effective beam width of the substantial effective beam widths of the first to third ultrasonic probes in the axial direction of the pipe or tube for a target flaw.

4. An ultrasonic testing apparatus, comprising:
an ultrasonic probe including n (n≧2) number of transducers arranged along a predetermined direction, disposed so as to face a test object; and
a transmission/reception control device for selecting m (n>m≧1) number of transducers from among the n number of transducers, transmitting ultrasonic waves from the selected m number of transducers toward the test object and receiving the ultrasonic waves therefrom, and switching m number of transducers to be selected successively,
wherein, if an angle that the arrangement direction of the n number of transducers makes with the surface of the test object which ultrasonic waves enter is θ(°), and the effective beam width of each selected m number of transducers with respect to a target flaw is W1 (mm), the transmission/reception control device switches m number of transducers to be selected successively by a switching pitch length P (mm) satisfying the following formula (1):

$$P \leq W1 \cdot \cos \theta \qquad (1)$$

and, in the transmission/reception control device, testing sensitivity is adjusted beforehand for each selected m number of transducers so that the highest echo intensities from target flaws received by each selected m number of transducers are approximately equivalent.

5. The ultrasonic testing apparatus according to claim 4, wherein
the n number of transducers included in the ultrasonic probe are arranged at an equal arrangement pitch of d (mm), and
if an angle that the arrangement direction of the n number of transducers makes with the surface of the test object which ultrasonic waves enter is θ(°), and the effective beam width of each selected m number of transducers with respect to a target flaw is W1 (mm), the transmission/reception control device switches m number of transducers to be selected successively by a switching pitch number K satisfying the following formula (2):

$$K \leq W1 \cdot \cos \theta \qquad (2).$$

6. An ultrasonic testing apparatus, comprising:
a first ultrasonic probe disposed so as to face a pipe or tube which is a test object, for detecting an axial flaw which is possible to occur in the pipe or tube;
a second ultrasonic probe disposed so as to face the pipe or tube for detecting a circumferential flaw which is possible to occur in the pipe or tube;
a third ultrasonic probe disposed so as to face the pipe or tube for detecting a lamination which is possible to occur in the pipe or tube;
a first transmission/reception control device for transmitting ultrasonic waves from a transducer included in the first ultrasonic probe toward the pipe or tube and receiving the ultrasonic waves therefrom;
a second transmission/reception control device for transmitting ultrasonic waves from a transducer included in the second ultrasonic probe toward the pipe or tube and receiving the ultrasonic waves therefrom;
a third transmission/reception control device for transmitting ultrasonic waves from a transducer included in the third ultrasonic probe toward the pipe or tube and receiving the ultrasonic waves therefrom; and
a driving device for rotating the pipe or tube in the circumferential direction and relatively moving the first to third ultrasonic probes in the axial direction of the pipe or tube,
wherein at least one ultrasonic probe selected from among the first to third ultrasonic probes is an ultrasonic probe including n (n≧2) number of transducers arranged along a predetermined direction so as to face the pipe or tube, and the arrangement direction of n number of transducers included in the selected ultrasonic probe is aligned with the axial direction of the pipe or tube;
the transmission/reception control device corresponding to the selected ultrasonic probe of the first to third transmission/reception control devices is the transmission/reception control device according to claim 4; and
the driving device rotates the pipe or tube in the circumferential direction and relatively moves the first to third ultrasonic probes in the axial direction of the pipe or tube so that the amount of relative displacement in the axial direction of the pipe or tube of the first to third ultrasonic probes per one turn of the pipe or tube is not larger than the minimum substantial effective beam width of the substantial effective beam widths of the first to third ultrasonic probes in the axial direction of the pipe or tube for a target flaw.

* * * * *